US00PP13035P2

(12) United States Plant Patent
Bergman

(10) Patent No.: US PP13,035 P2
(45) Date of Patent: Oct. 1, 2002

(54) CHRYSANTHEMUM PLANT NAMED 'YOSYLVIE'

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/955,840

(22) Filed: Sep. 20, 2001

(51) Int. Cl.[7] ..... A01H 5/00
(52) U.S. Cl. ..... Plt./294
(58) Field of Search ..... Plt./294

*Primary Examiner*—Bruce R. Campell
*Assistant Examiner*—Anne Marie Grünberg
(74) *Attorney, Agent, or Firm*—C. A. Whealy

(57) ABSTRACT

A distinct cultivar of Chrysanthemum plant named 'Yosylvie', characterized by its uniform, outwardly spreading and compact plant habit; strong and very freely branching growth habit; small green foliage; uniform and very freely flowering habit; early flowering, 6.5-week response time; small daisy-type inflorescences that are about 3.8 cm in diameter; white-colored ray florets and yellow-colored disc florets; good postproduction longevity with plants maintaining good substance and color for more than four weeks in an interior environment; and tolerance to high production temperatures.

2 Drawing Sheets

BACKGROUND OF THE INVENTION

The present Invention relates to a new and distinct cultivar of Chrysanthemum plant, botanically known as *Chrysanthemum×morifolium* and hereinafter referred to by the name 'Yosylvie'.

The new Chrysanthemum is a product of a planned breeding program conducted by the Inventor in Fort Myers, Fla. and Salinas, Calif. The objective of the breeding program is to create new compact potted Chrysanthemum cultivars that are suitable for year-round production with uniform plant growth habit, good vigor, small inflorescences with desirable inflorescence form and floret colors, fast response time, and good postproduction longevity.

The new Chrysanthemum originated from a cross made by the Inventor in May, 1997, in Salinas, Calif., of a proprietary Chrysanthemum seedling selection identified as code number YB-6500, not patented, as the female, or seed, parent with a proprietary Chrysanthemum seedling selection identified as code number YB-4207, not patented, as the male, or pollen, parent. The new Chrysanthemum was discovered and selected by the Inventor as a single flowering plant within the progeny of the stated cross grown in a controlled environment in Salinas, Calif. The selection of this plant was based on its uniform plant growth habit, desirable inflorescence form and floret colors, fast response time, and excellent postproduction longevity.

Asexual reproduction of the new Chrysanthemum by vegetative tip cuttings was first conducted in Fort Myers, Fla. in July, 1998. Asexual reproduction by cuttings has shown that the unique features of this new Chrysanthemum are stable and reproduced true to type in successive generations.

SUMMARY OF THE INVENTION

The cultivar Yosylvie has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Yosylvie'. These characteristics in combination distinguish 'Yosylvie' as a new and distinct Chrysanthemum:

1. Uniform, outwardly spreading and compact plant habit.
2. Strong and very freely branching growth habit.
3. Small green foliage.
4. Uniform and very freely flowering habit.
5. Typically grown as a spray-type.
6. Early flowering, 6.5-week response time.
7. Small daisy-type inflorescences that are about 3.8 cm in diameter.
8. White-colored ray florets and yellow-colored disc florets.
9. Good postproduction longevity with plants maintaining good substance and color for more than four weeks in an interior environment.
10. Tolerant to high production temperatures.

Plants of the new Chrysanthemum differ primarily from plants of the female parent selection in ray floret coloration as plants of the new Chrysanthemum have white ray florets whereas plants of the female parent selection have medium pink ray florets. In addition, plants of the new Chrysanthemum have smaller inflorescences than plants of the female selection.

Plants of the new Chrysanthemum differ primarily from plants of the male parent selection in ray floret coloration as plants of the new Chrysanthemum have white ray florets whereas plants of the male parent selection have light pink ray florets. In addition, plants of the new Chrysanthemum flower about 1.5 weeks earlier than plants of the male parent selection.

Plants of the new Chrysanthemum can be compared to plants of the cultivar White Cherie, disclosed in U.S. Plant Pat. No. 9,845. In side-by-side comparisons conducted by the Inventor in Salinas, Calif., plants of the new Chrysanthemum differed from plants of the cultivar White Cherie in the following characteristics:

1. Plants of the new Chrysanthemum flowered more uniformly than plants of the cultivar White Cherie.

2. Plants of the new Chrysanthemum flowered about 1.5 weeks earlier than plants of the cultivar White Cherie.
3. Plants of the new Chrysanthemum tolerated high production temperatures better than plants of the cultivar White Cherie.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which accurately describe the colors of the new Chrysanthemum.

The photograph on the first sheet comprises a side perspective view of a typical flowering plant of 'Yosylvie' grown as a spray-type.

The photograph on the second sheet comprises a close-up view of typical inflorescences of 'Yosylvie' grown as a spray-type.

DETAILED BOTANICAL DESCRIPTION

In the following description, color references are made to The Royal Horticultural Society Colour Chart except where general terms of ordinary dictionary significance are used. The following observations and measurements describe plants grown and flowered during the summer in Salinas, Calif., in a fiberglass-covered greenhouse and under conditions which approximate those generally used in commercial potted Chrysanthemum production. During the production of these plants, the following conditions were measured: day temperatures, 21 to 27° C.; night temperatures, 17 to 19° C.; and light levels, 5,000 to 6,000 foot-candles. Four unrooted cuttings were directly stuck in 15-cm containers, exposed to long day/short night conditions, and pinched once about 14 days later. One week after pinching, the photoinductive short day/long night treatments were started. Plants used for this description were grown as spray-types. Measurements and numerical values represent averages of typical flowering plants.

Botanical classification: *Chrysanthemum×morifolium* cultivar Yosylvie.

Commercial classification: Daisy-type potted Chrysanthemum.

Parentage:

*Female, or seed, parent.*—Proprietary *Chrysanthemum×morifolium* seedling selection identified as code number YB-6500, not patented.

*Male, or pollen, parent.*—Proprietary *Chrysanthemum×morifolium* seedling selection identified as code number YB-4207, not patented.

Propagation:

*Type.*—Terminal tip cuttings.

*Time to initiate roots.*—About four days at 21° C.

*Time to produce a rooted cutting.*—About ten days at 21° C.

*Root description.*—White, fibrous.

*Rooting habit.*—Freely branching.

Plant description:

*Appearance.*—Herbaceous daisy-type potted Chrysanthemum that is typically grown as a spray-type. Compact; stems outwardly spreading; uniform crown. Very freely branching, about seven or eight lateral branches develop after removal of terminal apex (pinching); dense and full plants.

*Plant height.*—About 28 cm.

*Plant width.*—About 49 cm.

*Lateral branches.*—Length: About 21 cm. Diameter: About 3.5 mm. Internode length: About 1.4 cm. Strength: Strong, flexible. Texture: Pubescent. Color: 144A.

*Foliage description.*—Arrangement: Alternate. Quanity of leaves per lateral stem: About 14 or 15. Length: About 4.9 cm. Width: About 3.1 cm. Apex: Cuspidate to mucronate. Base: Attenuate. Margin: Palmately lobed, sinuses between lateral lobes mostly divergent. Texture: Upper and lower surfaces with very fine pubescence; veins prominent on lower surface. Color: Young foliage, upper surface: 147A. Young foliage, lower surface: 147B. Mature foliage, upper surface: 146A. Mature foliage, lower surface: Close to 146B. Venation, upper surface: Close to 146A. Venation, lower surface: Close to 146B to 146C. Petiole length: About 2.4 cm. Petiole diameter: About 2.5 mm. Petiole color: Close to 146B to 146C.

Inflorescence description:

*Appearance.*—Daisy-type inflorescence form with elongated oblong-shaped ray florets. Inflorescences borne on terminals above foliage. Disk and ray florets arranged acropetally on a capitulum. Not fragrant. Typically grown as a spray-type.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering; plants exposed to three weeks of long day/short night conditions followed by photoinductive short day/long night conditions flower about 40 to 44 days later when grown during the summer and about 44 to 49 days later when grown during the winter.

*Postproduction longevity.*—Inflorescences maintain good color and substance for more than four weeks in an interior environment.

*Quantity of inflorescences.*—About 14 per lateral stem.

*Inflorescence bud.*—Height: About 4 mm. Diameter: About 5 mm. Color: Close to 144A.

*Inflorescence size.*—Diameter: About 3.8 cm. Depth (height): About 8 mm. Diameter of disc: About 9 mm. Receptacle diameter: About 4 mm.

*Ray florets.*—Shape: Elongated-oblong. Orientation: Initially upright, then about 70° from vertical. Aspect: Mostly flat and straight. Length: About 1.5 cm. Width: About 5 mm. Apex: Emarginate. Base: Attenuate; short corolla tube. Corolla tube length: About 3 mm. Margin: Entire. Texture: Smooth, glabrous, satiny. Number of ray florets per inflorescence: About 32 arranged in about two rows. Color: When opening and fully expanded, upper surface: Closest to 155D. When opening and fully expanded, lower surface: Closest to 155D.

*Disc florets.*—Arrangement: Massed at center of receptacle. Shape: Tubular, elongated. Apex: Five-pointed. Length: About 3 mm. Width: Apex: About 1 mm. Base: About 0.5 mm. Number of disc florets per inflorescence: About 114. Color: Immature: 154A to 5A. Mature: Apex: 5A to 7A. Mid-section and base: Closest to 155D.

*Peduncles.*—Length: First peduncle: About 5.6 cm. Fourth peduncle: About 5.5 cm. Seventh peduncle:

About 7.2 cm. Diameter: About 1.5 mm. Angle to vertical: About 30 to 35° from vertical. Strength: Moderately strong, flexible. Texture: Pubescent. Color: 144A.

*Reproductive organs.*—Androecium: Present on disc florets only. Anther color: 9A. Pollen: Not observed. Gynoecium: Present on both ray and disc florets.

*Seed.*—Seed production has not been observed.

Disease resistance: Resistance to pathogens common to Chrysanthemums has not been observed on plants grown under commercial greenhouse conditions.

High temperature tolerance: Plants of the new Chrysanthemum have been observed to be tolerant to high temperature conditions when grown during the summer under greenhouse conditions in southwest Florida.

It is claimed:

1. A new and distinct cultivar of Chrysanthemum plant named 'Yosylvie', as illustrated and described.

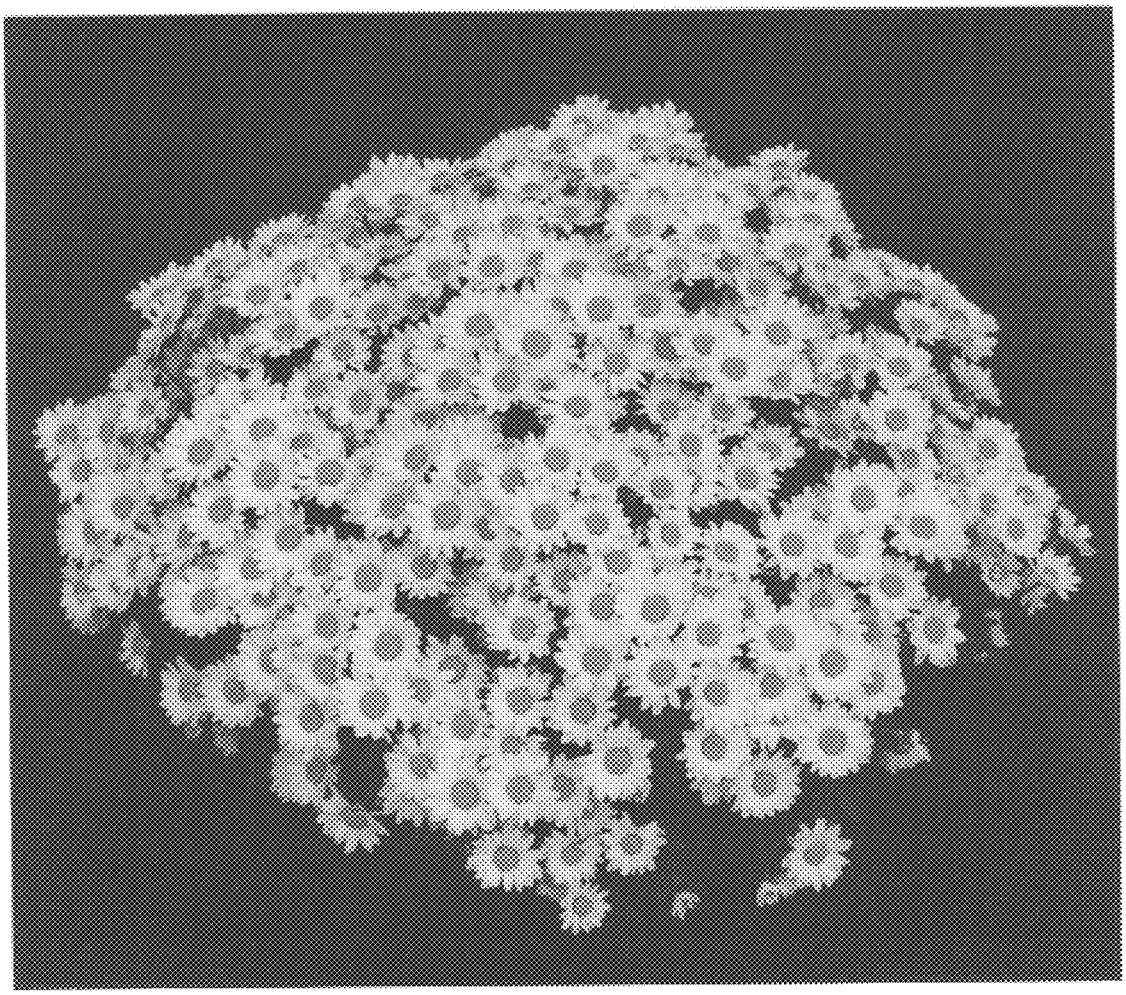

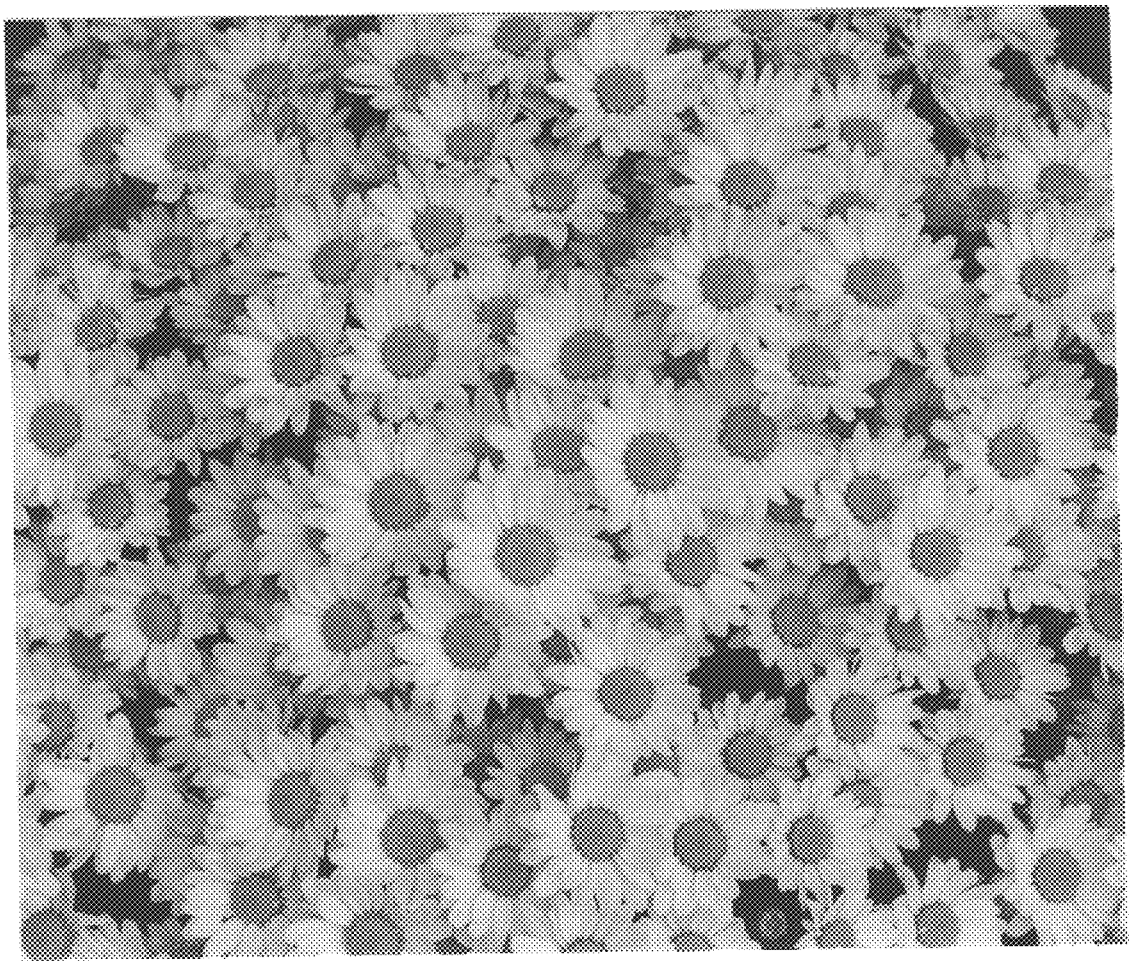

* * * * *